US011399763B2

(12) United States Patent
Honicker

(10) Patent No.: US 11,399,763 B2
(45) Date of Patent: Aug. 2, 2022

(54) SYSTEM AND METHOD FOR MAPPING CARDIAC MUSCLE FIBER ORIENTATION

(71) Applicant: St. Jude Medical, Cardiology Division, Inc., St. Paul, MN (US)

(72) Inventor: Myles Honicker, Jackson, MS (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 183 days.

(21) Appl. No.: 16/958,439

(22) PCT Filed: Jan. 3, 2019

(86) PCT No.: PCT/US2019/012176
§ 371 (c)(1),
(2) Date: Jun. 26, 2020

(87) PCT Pub. No.: WO2019/156755
PCT Pub. Date: Aug. 15, 2019

(65) Prior Publication Data
US 2021/0052178 A1 Feb. 25, 2021

Related U.S. Application Data

(60) Provisional application No. 62/629,394, filed on Feb. 12, 2018.

(51) Int. Cl.
*A61B 5/349* (2021.01)
*A61B 5/339* (2021.01)
*A61B 5/287* (2021.01)

(52) U.S. Cl.
CPC .............. *A61B 5/349* (2021.01); *A61B 5/339* (2021.01); *A61B 5/287* (2021.01)

(58) Field of Classification Search
None
See application file for complete search history.

(56) References Cited

U.S. PATENT DOCUMENTS 5,697,377 A 12/1997 Wittkampf
5,983,126 A 11/1999 Wittkampf
(Continued)

FOREIGN PATENT DOCUMENTS

JP H06-63025 A 3/1994
WO 2006/080349 A1 8/2006

OTHER PUBLICATIONS

Linnenbank et al., "How to measure propagation velocity in cardiac tissue: a simulation study," Jul. 22, 2014, Frontiers in Physiology, vol. 5, article 267, pp. 1-7. (Year: 2014).*

(Continued)

*Primary Examiner* — Kennedy Schaetzle
(74) *Attorney, Agent, or Firm* — Wiley Rein LLP

(57) ABSTRACT

Conduction velocity information for a cardiac region can be used to map the cardiac muscle fiber orientation of that region. In particular, for a plurality of locations within the cardiac region, a relationship between a local conduction velocity, a maximum local conduction velocity within the region, and a minimum local conduction velocity within the region is used to determine the cardiac muscle fiber orientation at the respective location. Even more particularly, when the local conduction velocity at the respective location equals the maximum local conduction velocity, the cardiac muscle fiber orientation is parallel to a direction of a conduction velocity vector at the respective location, and when the local conduction velocity at the respective location equals the minimum local conduction velocity, the cardiac muscle fiber orientation is perpendicular to a direction of a conduction velocity vector at the respective location.

20 Claims, 5 Drawing Sheets

(56) References Cited

U.S. PATENT DOCUMENTS

| | | |
|---|---|---|
| 6,640,119 B1 | 10/2003 | Budd et al. |
| 6,728,562 B1 | 4/2004 | Budd et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,263,397 B2 | 8/2007 | Hauck et al. |
| 7,885,707 B2 | 2/2011 | Hauck |
| 10,485,510 B2* | 11/2019 | Mansi .................. A61B 8/5246 |
| 2014/0122048 A1* | 5/2014 | Vadakkumpadan ......................... A61B 5/7275 703/11 |
| 2015/0228254 A1 | 8/2015 | Olson |
| 2017/0027465 A1 | 2/2017 | Blauer et al. |

OTHER PUBLICATIONS

International Search Report and Written Opinion for PCT/US2019/012176, dated Apr. 2, 2019.

\* cited by examiner

SYSTEM AND METHOD FOR MAPPING CARDIAC MUSCLE FIBER ORIENTATION

CROSS-REFERENCE TO RELATED APPLICATIONS

This application claims the benefit of U.S. provisional application No. 62/629,394, filed 12 Feb. 2018, which is hereby incorporated by reference as though fully set forth herein.

BACKGROUND

The present disclosure relates generally to electrophysiological mapping, such as may be performed in cardiac diagnostic and therapeutic procedures. In particular, the present disclosure relates to systems, apparatuses, and methods for mapping the orientation of cardiac muscle fibers.

Electrophysiological mapping, and more particularly electrocardiographic mapping, is a part of numerous cardiac diagnostic and therapeutic procedures. As the complexity of such procedures increases, however, the electrophysiology maps utilized must increase in quality, in density, and in the rapidity and ease with which they can be generated.

In certain electrophysiology studies, it can be desirable for the practitioner to know the orientation of cardiac muscle fibers. For instance, if the practitioner knows cardiac muscle fiber orientation, he or she may be able to more readily detect the location of arrhythmic circuits even when the patient is not arrhythmic. As another example, the practitioner can use cardiac muscle fiber orientation to visualize connection from one muscle substrate to another (e.g., pulmonary vein connections, superior vena cava connections, accessory pathways, and interfaces between scar and normal tissue).

BRIEF SUMMARY

Disclosed herein is a method of mapping cardiac muscle fiber orientation, including: receiving, at an electroanatomical mapping system, a conduction velocity map for a cardiac region; identifying a maximum local conduction velocity within the cardiac region and a minimum local conduction velocity within the cardiac region using the conduction velocity map; computing a min-max conduction velocity ratio of the minimum local conduction velocity within the cardiac region to the maximum local conduction velocity within the cardiac region; and, for a plurality of locations within the cardiac region: identifying a local conduction velocity at the respective location within the cardiac region using the conduction velocity map; computing a local conduction velocity ratio of the local conduction velocity at the respective location within the cardiac region to the maximum local conduction velocity within the cardiac region; and determining a cardiac muscle fiber orientation at the respective location within the cardiac region using the local conduction velocity ratio, thereby generating a cardiac muscle fiber orientation map.

The step of determining a cardiac muscle fiber orientation at the respective location within the cardiac region using the local conduction velocity ratio can include assigning a cardiac muscle fiber orientation to the respective location within the cardiac region according to a relationship between the local conduction velocity ratio, the min-max conduction velocity ratio, and 1. For instance, it can be appropriate to assign a cardiac muscle fiber orientation to the respective location within the cardiac region that is parallel to a direction of a conduction velocity vector at the respective location within the cardiac region when the local conduction velocity ratio equals 1, to assign a cardiac muscle fiber orientation to the respective location within the cardiac region that is perpendicular to the direction of the conduction velocity vector at the respective location within the cardiac region when the local conduction velocity ratio equals the min-max conduction velocity ratio, and/or to interpolate (e.g., linearly interpolate) the cardiac muscle fiber orientation at the respective location within the cardiac region according to the relationship between the local conduction velocity ratio, the min-max conduction velocity ratio, and 1.

In aspects of the disclosure, the method also includes outputting a graphical representation of the cardiac muscle fiber orientation map on a three-dimensional geometric model of the cardiac region. Optionally, the method can also include outputting a graphical representation of the conduction velocity map on the three-dimensional geometric model of the cardiac region.

Also disclosed herein is a method of mapping cardiac muscle fiber orientation for a cardiac region from conduction velocity information for the cardiac region, the method including: for a plurality of locations within the cardiac region, determining a cardiac muscle fiber orientation at the respective location within the cardiac region based on a relationship between a local conduction velocity at the respective location within the cardiac region, a maximum local conduction velocity within the cardiac region, and a minimum local conduction velocity within the cardiac region, thereby generating a cardiac muscle fiber orientation map. The method can also include outputting a graphical representation of the cardiac muscle fiber orientation map on a three-dimensional geometric model of the cardiac region and/or outputting a graphical representation of the conduction velocity information on the three-dimensional model of the cardiac region.

The step of determining a cardiac muscle fiber orientation at the respective location within the cardiac region can include assigning a cardiac muscle fiber orientation to the respective location within the cardiac region that is parallel to a direction of a conduction velocity vector at the respective location within the cardiac region when the local conduction velocity at the respective location within the cardiac region equals the maximum local conduction velocity within the cardiac region. Similarly, the step of determining a cardiac muscle fiber orientation at the respective location within the cardiac region can include assigning a cardiac muscle fiber orientation to the respective location within the cardiac region that is perpendicular to a direction of a conduction velocity vector at the respective location within the cardiac region when the local conduction velocity at the respective location within the cardiac region equals the minimum local conduction velocity within the cardiac region. In still other embodiments of the disclosure, the step of determining a cardiac muscle fiber orientation at the respective location within the cardiac region can include assigning a cardiac muscle fiber orientation to the respective location within the cardiac region that is between parallel to a direction of a conduction velocity vector at the respective location within the cardiac region and perpendicular to the direction of the conduction velocity vector at the respective location when the local conduction velocity at the respective location within the cardiac region is between the minimum local conduction velocity within the cardiac region and the maximum local conduction velocity within the cardiac region. For instance, the cardiac muscle fiber orientation assigned to the respective location within the cardiac region can be determined via interpolation, such as linear interpolation.

It is also contemplated that the step of determining a cardiac muscle fiber orientation at the respective location within the cardiac region based on a relationship between a local conduction velocity at the respective location within the cardiac region, a maximum local conduction velocity within the cardiac region, and a minimum local conduction velocity within the cardiac region can include determining the cardiac muscle fiber orientation based on a relationship between a ratio of the local conduction velocity at the respective location within the cardiac region and the maximum local conduction velocity within the cardiac region, a ratio of the minimum local conduction velocity within the cardiac region and the maximum local conduction velocity within the cardiac region, and 1.

The instant disclosure also provides a system for mapping cardiac muscle fiber orientation, including: a muscle fiber orientation processor configured to: receive a conduction velocity map for a cardiac region; identify a maximum local conduction velocity within the cardiac region and a minimum local conduction velocity within the cardiac region using the conduction velocity map; and, for a plurality of locations within the cardiac region: identify a local conduction velocity at the respective location within the cardiac region using the conduction velocity map; and determine a cardiac muscle fiber orientation at the respective location within the cardiac region based upon a relationship between the local conduction velocity at the respective location within the cardiac region, the maximum local conduction velocity within the cardiac region, and the minimum local conduction velocity within the cardiac region, thereby generating a cardiac muscle fiber orientation map. Optionally, the system can also include a mapping processor configured to output a graphical representation of the cardiac muscle fiber orientation map on a three-dimensional geometric model of the cardiac region and/or to output a graphical representation of the conduction velocity information on the three-dimensional model of the cardiac region.

According to aspects of the disclosure, the muscle fiber orientation processor is configured to determine the cardiac muscle fiber orientation at the respective location within the cardiac region by comparing a ratio of the local conduction velocity at the respective location within the cardiac region to the maximum local conduction velocity within the cardiac region and a ratio of the minimum conduction velocity at the respective location within the cardiac region to the maximum local conduction velocity within the cardiac region.

In other aspects of the disclosure, the muscle fiber orientation processor is configured to determine that the cardiac muscle fiber orientation at the respective location within the cardiac region is parallel to a direction of a conduction velocity vector at the respective location within the cardiac region when the local conduction velocity at the respective location within the cardiac region equals the maximum local conduction velocity within the cardiac region; and to determine that the cardiac muscle fiber orientation at the respective location within the cardiac region is perpendicular to a direction of a conduction velocity vector at the respective location within the cardiac region when the local conduction velocity at the respective location within the cardiac region equals the minimum local conduction velocity within the cardiac region.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides systems, apparatuses, and methods for the creation of electrophysiology maps (e.g., electrocardiographic maps) that provide information regarding the orientation of cardiac muscle fibers (referred to herein as "cardiac muscle fiber orientation maps"). For purposes of illustration, aspects of the disclosure will be described in detail herein in the context of a cardiac mapping procedure carried out using an electrophysiology mapping system (e.g., using an electroanatomical mapping system such as the EnSite Precision™ cardiac mapping system from Abbott Laboratories).

Figure 1:
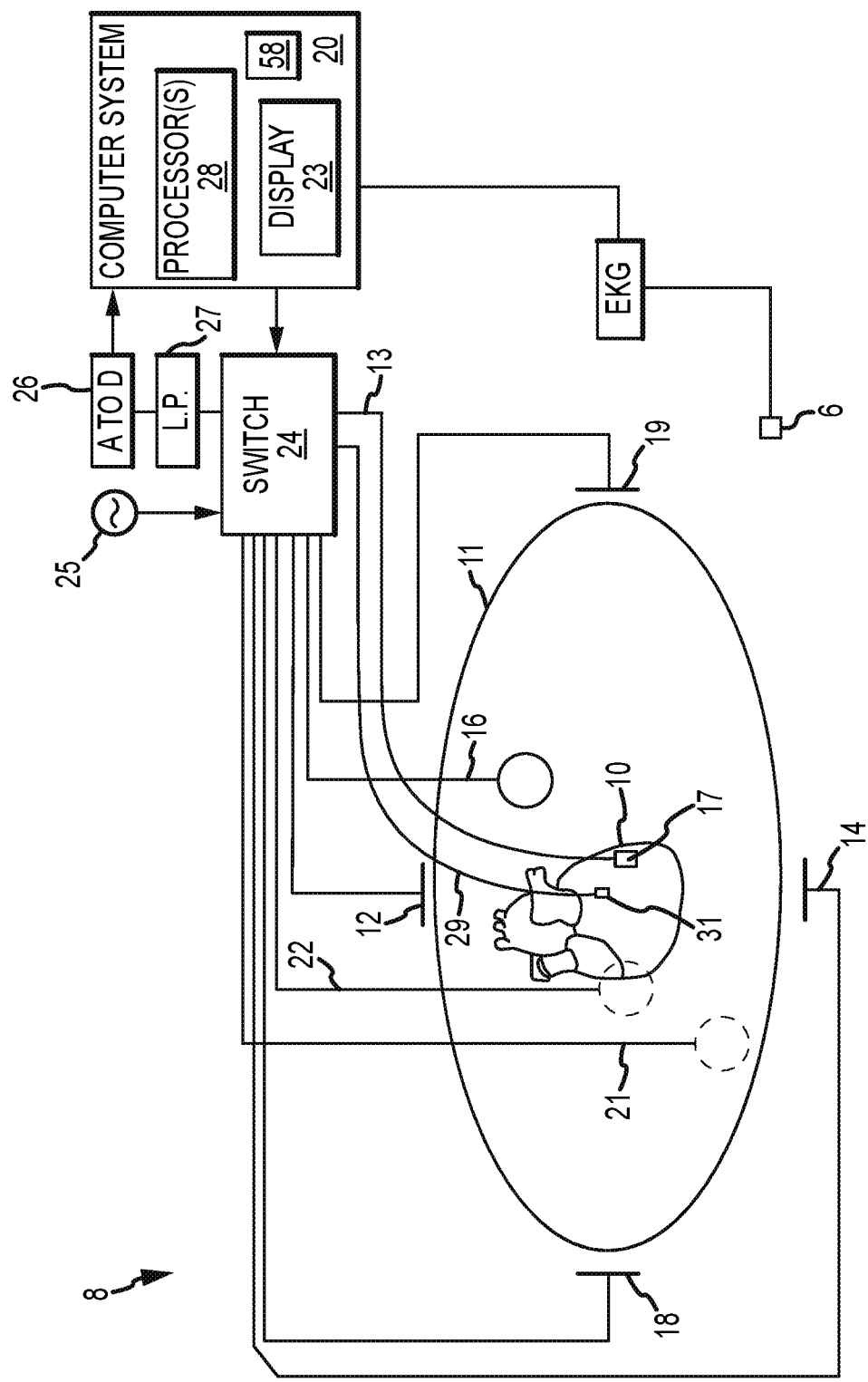
FIG. 1 is a schematic diagram of an exemplary electroanatomical mapping system.

FIG. 1 shows a schematic diagram of an exemplary electroanatomical mapping system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, and as will be further described below, system 8 determines the location, and in some aspects the orientation, of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only a single lead 6 and its connection to computer 20 is illustrated in FIG. 1.

A representative catheter 13 having at least one electrode 17 is also shown. This representative catheter electrode 17 is referred to as the "roving electrode," "moving electrode," or "measurement electrode" throughout the specification. Typically, multiple electrodes 17 on catheter 13, or on multiple such catheters, will be used. In one embodiment, for example, the system 8 may comprise sixty-four electrodes on twelve catheters disposed within the heart and/or vasculature of the patient. In other embodiments, system 8 may utilize a single catheter that includes multiple (e.g., eight) splines, each of which in turn includes multiple (e.g., eight) electrodes.

The foregoing embodiments are merely exemplary, however, and any number of electrodes and/or catheters may be used. For example, in some embodiments, a high density mapping catheter, such as the Ensite™ Array™ non-contact mapping catheter or Advisor™ HD grid mapping catheter, both of Abbott Laboratories, can be utilized.

Figure 2:
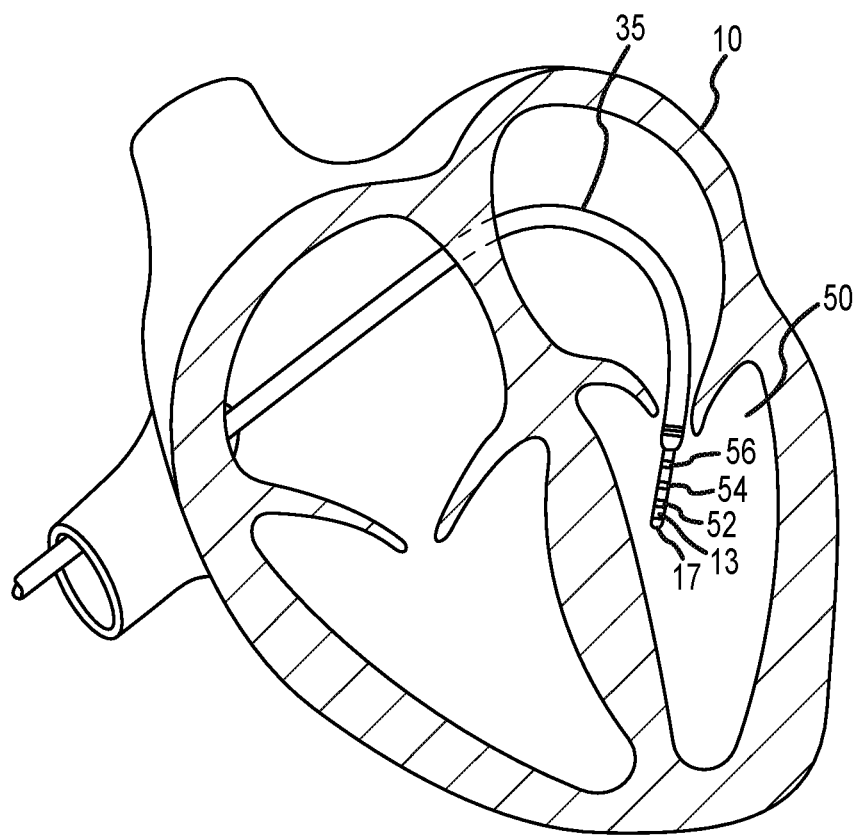
FIG. 2 depicts an exemplary catheter that can be used in connection with aspects of the instant disclosure.

Likewise, it should be understood that catheter 13 (or multiple such catheters) are typically introduced into the heart and/or vasculature of the patient via one or more introducers and using familiar procedures. For purposes of this disclosure, a segment of an exemplary catheter 13 is shown in FIG. 2. In FIG. 2, catheter 13 extends into the left ventricle 50 of the patient's heart 10 through a transseptal sheath 35. The use of a transseptal approach to the left ventricle is well known and will be familiar to those of ordinary skill in the art, and need not be further described herein. Of course, catheter 13 can also be introduced into the heart in any other suitable manner.

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by system 8.

Similarly, each of electrodes 17, 52, 54, and 56 can be used to gather electrophysiological data from the cardiac surface (e.g., surface electrograms). The ordinarily skilled artisan will be familiar with various modalities for the acquisition and processing of electrophysiology data points (including, for example, both contact and non-contact electrophysiological mapping), such that further discussion thereof is not necessary to the understanding of the techniques disclosed herein. Likewise, various techniques familiar in the art can be used to generate a graphical representation of a cardiac geometry and/or of cardiac electrical activity from the plurality of electrophysiology data points. Moreover, insofar as the ordinarily skilled artisan will appreciate how to create electrophysiology maps from electrophysiology data points, the aspects thereof will only be described herein to the extent necessary to understand the present disclosure.

Returning now to FIG. 1, in some embodiments, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20 may comprise, for example, a conventional general-purpose computer, a special-purpose computer, a distributed computer, or any other type of computer. The computer 20 may comprise one or more processors 28, such as a single central processing unit ("CPU"), or a plurality of processing units, commonly referred to as a parallel processing environment, which may execute instructions to practice the various aspects described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17 placed in the heart 10 are exposed to the field from a current pulse and are measured with respect to ground, such as belly patch 21. In practice the catheters within the heart 10 may contain more or fewer electrodes than the sixteen shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which system 8 measures positions. Data sets from each of the surface electrodes, the internal electrodes, and the virtual electrodes may all be used to determine the location of the roving electrodes 17 within heart 10.

The measured voltages may be used by system 8 to determine the location in three-dimensional space of the electrodes inside the heart, such as roving electrodes 17 relative to a reference location, such as reference electrode 31. That is, the voltages measured at reference electrode 31 may be used to define the origin of a coordinate system, while the voltages measured at roving electrodes 17 may be used to express the location of roving electrodes 17 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described, for example, in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ or EnSite Precision™ cardiac mapping and visualization system of Abbott Laboratories. Other localization systems, however, may be used in connection with the present teachings, including for example the RHYTHMIA HDX™ mapping system of Boston Scientific Corporation, the CARTO navigation and location system of Biosense Webster, Inc., the AURORA® system of Northern Digital Inc., Sterotaxis' NIOBE® Magnetic Navigation System, as well as MediGuide™ Technology from Abbott Laboratories.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

Aspects of the disclosure relate to mapping cardiac muscle fiber orientation, and, more particularly to mapping cardiac muscle fiber orientation using conduction velocity information (e.g., a conduction velocity map for a cardiac region). Accordingly, system 8 can also include a muscle fiber orientation module 58. Muscle fiber orientation module 58 can be used, inter alia, to determine the orientation of a cardiac muscle fiber from conduction velocity information, as discussed in detail below.

Figure 3:
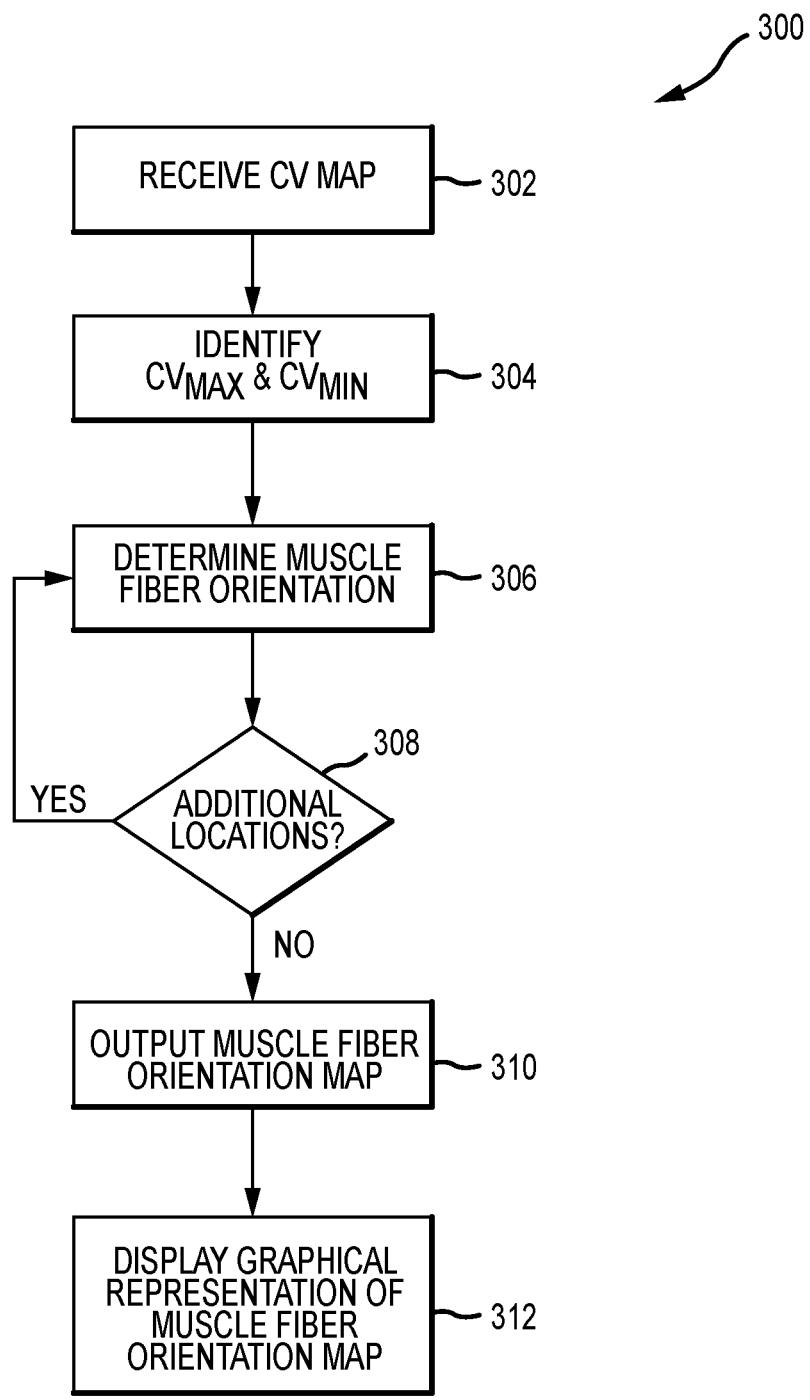
FIG. 3 is a flowchart of representative steps that can be followed according to exemplary embodiments disclosed herein.

One exemplary method of determining cardiac muscle fiber orientation and generating a cardiac muscle fiber orientation map according to the present teachings will be explained with reference to the flowchart 300 of representative steps presented as FIG. 3. In some embodiments, for example, flowchart 300 may represent several exemplary steps that can be carried out by electroanatomical mapping system 8 of FIG. 1 (e.g., by processor 28 and/or muscle fiber orientation module 58). It should be understood that the representative steps described below can be either hardware- or software-implemented. For the sake of explanation, the term "signal processor" is used herein to describe both hardware- and software-based implementations of the teachings herein.

In block 302, system 8 receives a conduction velocity map for a cardiac region. Those of ordinary skill in the art will be familiar with the creation of conduction velocity maps. By way of example only, however, U.S. application No. 62/478,377, which is hereby incorporated by reference as though fully set forth herein, describes various exemplary systems and methods for mapping local conduction velocity, including determining the direction of a cardiac activation wavefront.

In block 304, system 8 identifies a maximum local conduction velocity ($CV_{max}$) within the cardiac region and a minimum local conduction velocity ($CV_{min}$) within the cardiac region. Optionally, system 8 can also compute a min-max conduction velocity ratio $CV_{min}/CV_{max}$.

In block 306, system 8 determines the orientation of the cardiac muscle fiber at a point within the cardiac region. The instant teachings leverage that conduction velocity is highest along the longitudinal axis of the heart muscle and lowest perpendicular to the longitudinal axis of the heart muscle. Thus, system 8 can utilize a relationship between the following values to determine the orientation of the cardiac muscle fiber at a given point within the cardiac region: the local conduction velocity ($CV_{loc}$) at the point within the cardiac region; $CV_{max}$; and $CV_{min}$.

In one aspect of the disclosure, the orientation of the cardiac muscle fiber at the point can be determined using a local conduction velocity ratio $CV_{loc}/CV_{max}$. Specifically, the closer the local conduction velocity ratio is to 1, then the closer the cardiac muscle fiber orientation is to parallel to the direction of the conduction velocity vector. If the local conduction velocity ratio equals 1, then the cardiac muscle fiber is oriented parallel to the direction of the conduction velocity vector.

Conversely, the closer the local conduction velocity is to the min-max conduction velocity ratio, then the closer the cardiac muscle fiber orientation is to perpendicular of the direction of the conduction velocity vector. If the local conduction velocity ratio equals the min-max conduction velocity ratio, then the cardiac muscle fiber is oriented perpendicular to the direction of the conduction velocity vector.

When the local conduction velocity ratio is between 1 and the min-max conduction velocity ratio, the orientation of the cardiac muscle fiber will likewise be between parallel to and perpendicular to the direction of the conduction velocity vector. The specific orientation can be determined, for example, using interpolation, such as linear interpolation (e.g., if the local conduction velocity ratio is about halfway between 1 and the min-max conduction velocity ratio, the orientation of the cardiac muscle fiber is at about 45 degrees to the direction of the conduction velocity vector and so forth).

In another aspect of the disclosure, the orientation of the cardiac muscle fiber at the point can be determined by comparing the value of $CV_{loc}$ to both $CV_{max}$ and $CV_{min}$. Specifically, the closer $CV_{loc}$ is to $CV_{max}$, then the closer the cardiac muscle fiber orientation is to parallel to the direction of the conduction velocity vector. If $CV_{loc}$ equals $CV_{max}$, then the cardiac muscle fiber is oriented parallel to the direction of the conduction velocity vector.

Conversely, the closer $CV_{loc}$ is to $CV_{min}$, then the closer the cardiac muscle fiber orientation is to perpendicular to the direction of the conduction velocity vector. If $CV_{loc}$ equals then the cardiac muscle fiber is oriented perpendicular to the direction of the conduction velocity vector.

When $CV_{min} < CV_{loc} < CV_{max}$, the orientation of the cardiac muscle fiber will likewise be between parallel to and perpendicular to the direction of the conduction velocity vector. The specific orientation can be determined, for example, using interpolation (e.g., if $CV_{loc}$ is about halfway between $CV_{min}$ and $CV_{max}$, then the orientation of the cardiac muscle fiber is at about 45 degrees to the direction of the conduction velocity vector, and so forth).

Decision block 308 considers whether there are additional locations at which to determine cardiac muscle fiber orientation. If so, block 306 repeats. If not, a cardiac muscle fiber orientation map is output in block 310.

In block 312, a graphical representation of the cardiac muscle fiber orientation map can be output on a three-dimensional geometric model of the cardiac region, for example on display 23. Optionally, a graphical representation of the conduction velocity map can also be output on the same three-dimensional model, thereby allowing the practitioner to simultaneously visualize cardiac muscle fiber orientation and the cardiac activation wavefront.

Figure 4A:
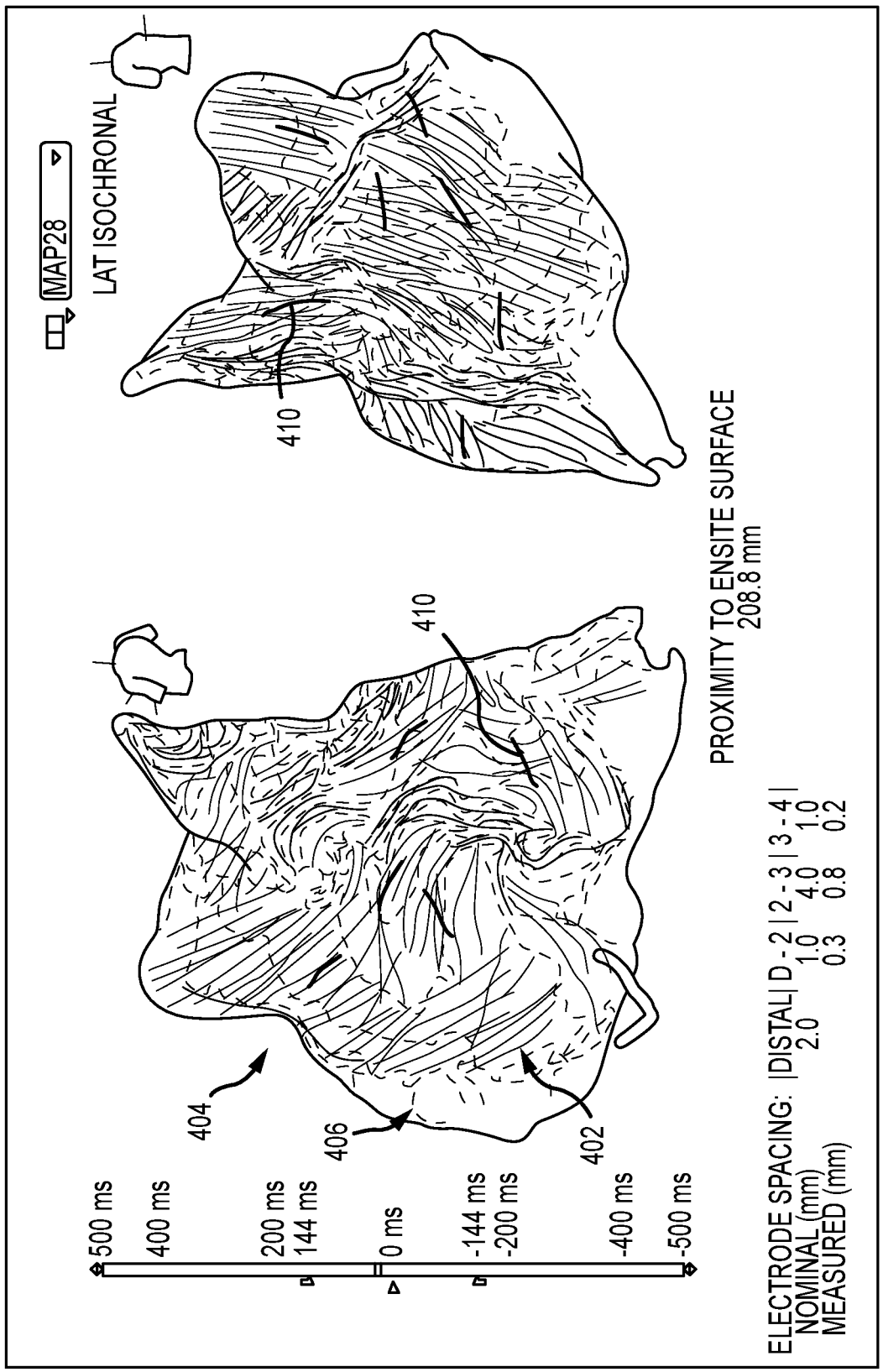
FIGS. 4A and 4B illustrate graphical representations of cardiac muscle fiber orientation maps according to the instant disclosure.
Figure 4B:
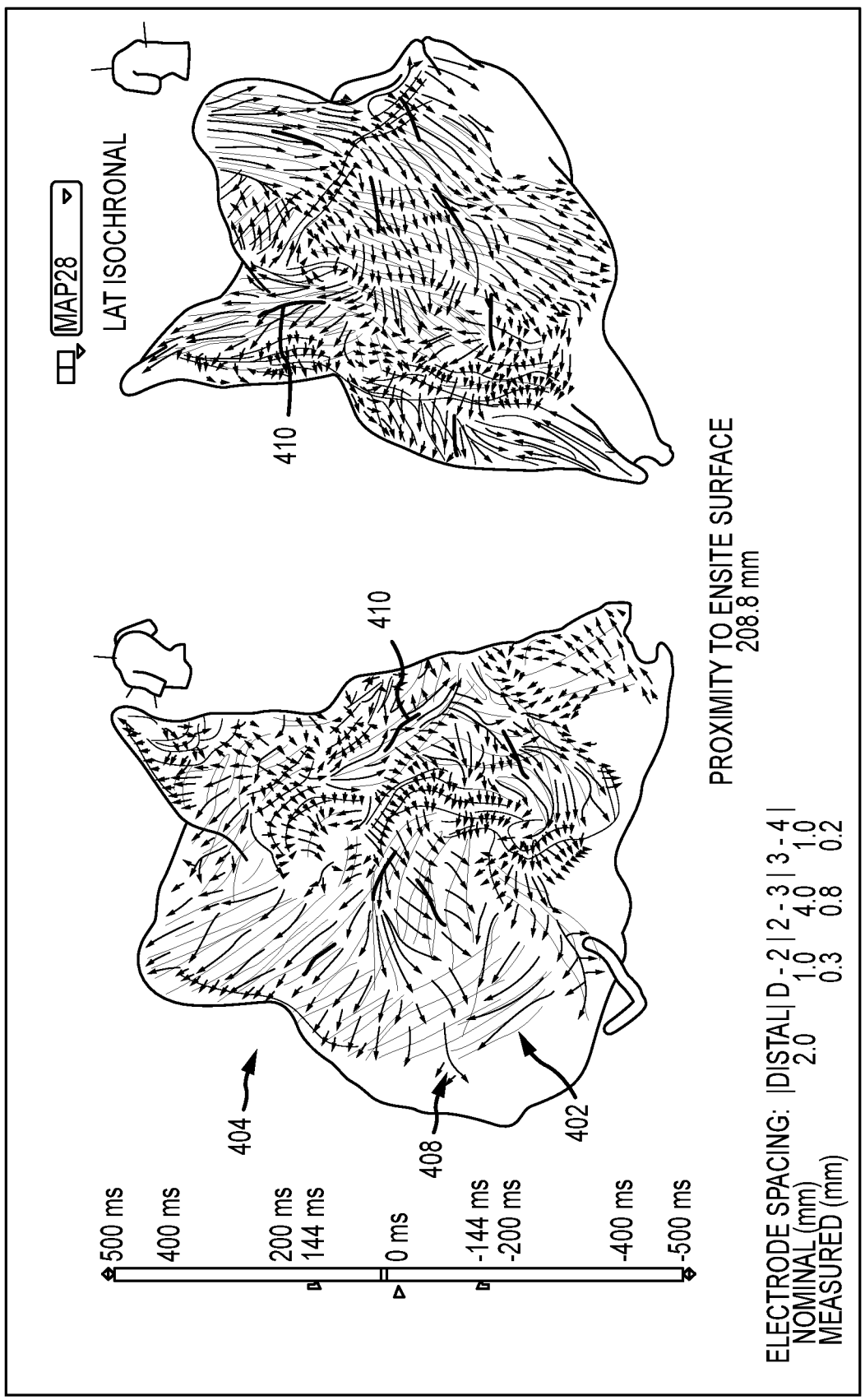

FIGS. 4A and 4B are illustrative graphical representations of cardiac muscle fiber orientation maps according to the foregoing teachings. FIGS. 4A and 4B show a common graphical representation of cardiac muscle fiber orientation in the form of striations 402 drawn on a three-dimensional cardiac model 404. Both FIGS. 4A and 4B also show a graphical representation of the conduction velocity map used to determine the cardiac muscle fiber orientation map. FIG. 4A depicts isochrones 406, while FIG. 4B depicts conduction velocity vectors 408. FIGS. 4A and 4B also depict tape measure markers 410, at 10 mm intervals, which allow a practitioner to gauge distances on the cardiac muscle fiber orientation maps.

As shown in FIG. 4B, where conduction velocity vectors 408 are longer, representative of higher local conduction velocity, they are generally closer to parallel to the cardiac muscle fiber orientation striations 402. Conversely, where conduction velocity vectors 408 are shorter, representative of lower local conduction velocity, they are generally closer to perpendicular to the cardiac muscle fiber orientation striations 402.

Although several embodiments have been described above with a certain degree of particularity, those skilled in the art could make numerous alterations to the disclosed embodiments without departing from the spirit or scope of this invention.

For example, the teachings herein can be applied in real time (e.g., during an electrophysiology study) or during post-processing (e.g., to electrophysiology data points collected during an electrophysiology study performed at an earlier time).

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of mapping cardiac muscle fiber orientation, comprising:
   receiving, at an electroanatomical mapping system, a conduction velocity map for a cardiac region;
   identifying a maximum local conduction velocity within the cardiac region and a minimum local conduction velocity within the cardiac region using the conduction velocity map;
   computing a min-max conduction velocity ratio of the minimum local conduction velocity within the cardiac region to the maximum local conduction velocity within the cardiac region; and
   for a plurality of locations within the cardiac region:
      identifying a local conduction velocity at the respective location within the cardiac region using the conduction velocity map;
      computing a local conduction velocity ratio of the local conduction velocity at the respective location within the cardiac region to the maximum local conduction velocity within the cardiac region;
      determining a cardiac muscle fiber orientation at the respective location within the cardiac region using the local conduction velocity ratio; and generating a cardiac muscle fiber orientation map.

2. The method according to claim 1, wherein determining a cardiac muscle fiber orientation at the respective location within the cardiac region using the local conduction velocity ratio comprises assigning a cardiac muscle fiber orientation to the respective location within the cardiac region according to a relationship between the local conduction velocity ratio, the min-max conduction velocity ratio, and 1.

3. The method according to claim 2, wherein assigning a cardiac muscle fiber orientation to the respective location within the cardiac region according to a relationship between the local conduction velocity ratio, the min-max conduction velocity ratio, and 1 comprises assigning a cardiac muscle fiber orientation to the respective location within the cardiac region that is parallel to a direction of a conduction velocity vector at the respective location within the cardiac region when the local conduction velocity ratio equals 1.

4. The method according to claim 2, wherein assigning a cardiac muscle fiber orientation to the respective location within the cardiac region according to a relationship between the local conduction velocity ratio, the min-max conduction velocity ratio, and 1 comprises assigning a cardiac muscle fiber orientation to the respective location within the cardiac region that is perpendicular to the direction of the conduction velocity vector at the respective location within the cardiac region when the local conduction velocity ratio equals the min-max conduction velocity ratio.

5. The method according to claim 2, wherein assigning a cardiac muscle fiber orientation to the respective location within the cardiac region according to a relationship between the local conduction velocity ratio, the min-max conduction velocity ratio, and 1 comprises interpolating the cardiac muscle fiber orientation at the respective location within the cardiac region according to the relationship between the local conduction velocity ratio, the min-max conduction velocity ratio, and 1.

6. The method according to claim 1, further comprising outputting a graphical representation of the cardiac muscle fiber orientation map on a three-dimensional geometric model of the cardiac region.

7. The method according to claim 6, further comprising outputting a graphical representation of the conduction velocity map on the three-dimensional geometric model of the cardiac region.

8. A method of mapping cardiac muscle fiber orientation for a cardiac region from conduction velocity information for the cardiac region, the method comprising:
for a plurality of locations within the cardiac region, determining a cardiac muscle fiber orientation at the respective location within the cardiac region based on a relationship between a local conduction velocity at the respective location within the cardiac region, a maximum local conduction velocity within the cardiac region, and a minimum local conduction velocity within the cardiac region, and generating a cardiac muscle fiber orientation map.

9. The method according to claim 8, further comprising outputting a graphical representation of the cardiac muscle fiber orientation map on a three-dimensional geometric model of the cardiac region.

10. The method according to claim 9, further comprising outputting a graphical representation of the conduction velocity information on the three-dimensional model of the cardiac region.

11. The method according to claim 8, wherein determining a cardiac muscle fiber orientation at the respective location within the cardiac region comprises assigning a cardiac muscle fiber orientation to the respective location within the cardiac region that is parallel to a direction of a conduction velocity vector at the respective location within the cardiac region when the local conduction velocity at the respective location within the cardiac region equals the maximum local conduction velocity within the cardiac region.

12. The method according to claim 8, wherein determining a cardiac muscle fiber orientation at the respective location within the cardiac region comprises assigning a cardiac muscle fiber orientation to the respective location within the cardiac region that is perpendicular to a direction of a conduction velocity vector at the respective location within the cardiac region when the local conduction velocity at the respective location within the cardiac region equals the minimum local conduction velocity within the cardiac region.

13. The method according to claim 8, wherein determining a cardiac muscle fiber orientation at the respective location within the cardiac region comprises assigning a cardiac muscle fiber orientation to the respective location within the cardiac region that is between parallel to a direction of a conduction velocity vector at the respective location within the cardiac region and perpendicular to the direction of the conduction velocity vector at the respective location when the local conduction velocity at the respective location within the cardiac region is between the minimum local conduction velocity within the cardiac region and the maximum local conduction velocity within the cardiac region.

14. The method according to claim 13, wherein the cardiac muscle fiber orientation assigned to the respective location within the cardiac region is determined via linear interpolation.

15. The method according to claim 8, wherein determining a cardiac muscle fiber orientation at the respective location within the cardiac region based on a relationship between a local conduction velocity at the respective location within the cardiac region, a maximum local conduction velocity within the cardiac region, and a minimum local conduction velocity within the cardiac region comprises determining the cardiac muscle fiber orientation based on a relationship between a ratio of the local conduction velocity at the respective location within the cardiac region and the maximum local conduction velocity within the cardiac region, a ratio of the minimum local conduction velocity within the cardiac region and the maximum local conduction velocity within the cardiac region, and 1.

16. A system for mapping cardiac muscle fiber orientation, comprising:
a muscle fiber orientation module configured to:
receive a conduction velocity map for a cardiac region;
identify a maximum local conduction velocity within the cardiac region and a minimum local conduction velocity within the cardiac region using the conduction velocity map; and
for a plurality of locations within the cardiac region:
identify a local conduction velocity at the respective location within the cardiac region using the conduction velocity map;
determine a cardiac muscle fiber orientation at the respective location within the cardiac region based upon a relationship between the local conduction velocity at the respective location within the cardiac region, the maximum local conduction velocity within the cardiac region, and the minimum local conduction velocity within the cardiac region; and generate a cardiac muscle fiber orientation map.

17. The system according to claim 16, further comprising a mapping processor configured to output a graphical representation of the cardiac muscle fiber orientation map on a three-dimensional geometric model of the cardiac region.

18. The system according to claim 17, wherein the mapping processor is further configured to output a graphical representation of the conduction velocity information on the three-dimensional model of the cardiac region.

19. The system according to claim 16, wherein the muscle fiber orientation processor is configured to determine the cardiac muscle fiber orientation at the respective location within the cardiac region by comparing a ratio of the local conduction velocity at the respective location within the cardiac region to the maximum local conduction velocity within the cardiac region and a ratio of the minimum conduction velocity at the respective location within the cardiac region to the maximum local conduction velocity within the cardiac region.

20. The system according to claim 16, wherein the muscle fiber orientation processor is configured:

to determine that the cardiac muscle fiber orientation at the respective location within the cardiac region is parallel to a direction of a conduction velocity vector at the respective location within the cardiac region when the local conduction velocity at the respective location within the cardiac region equals the maximum local conduction velocity within the cardiac region; and to determine that the cardiac muscle fiber orientation at the respective location within the cardiac region is perpendicular to a direction of a conduction velocity vector at the respective location within the cardiac region when the local conduction velocity at the respective location within the cardiac region equals the minimum local conduction velocity within the cardiac region.

* * * * *